United States Patent [19]

Makoui et al.

[11] Patent Number: 4,689,118

[45] Date of Patent: Aug. 25, 1987

[54] CROSS-LINKED PORE CONTAINING MICROFIBRILLATED CELLULOSE PREPARED BY FREEZING AND SOLVENT EXCHANGE

[75] Inventors: Kambiz B. Makoui, Menasha, Wis.; Pronoy K. Chatterjee, Spotswood, N.J.

[73] Assignee: Personal Products Company, Milltown, N.J.

[21] Appl. No.: 757,569

[22] Filed: Jul. 22, 1985

[51] Int. Cl.[4] .................... D21D 3/00; D21F 3/00; D21H 3/00; D21J 3/00

[52] U.S. Cl. .................... 162/100; 162/9; 162/102; 162/158; 162/164.3; 162/182; 604/369; 604/374

[58] Field of Search ............. 604/368, 369, 374–378, 604/904; 162/9, 100, 158, 164.3, 182, 102

[56] References Cited

U.S. PATENT DOCUMENTS

| | | | |
|---|---|---|---|
| Re. 30,029 | 6/1979 | Smith | 604/376 |
| 3,005,457 | 10/1967 | Millman et al. | 604/375 |
| 3,224,926 | 12/1965 | Bernardin | 604/368 |
| 3,339,550 | 9/1967 | Van Haaften | 604/375 |
| 3,589,364 | 6/1971 | Dean et al. | 604/376 |
| 3,618,607 | 11/1971 | Ellis et al. | 604/368 |
| 3,658,790 | 4/1972 | Bernardin | 604/375 |
| 3,671,184 | 6/1972 | Cuculo | 604/376 |
| 3,691,154 | 9/1972 | Bernardin | 604/368 |
| 3,723,413 | 3/1973 | Chatterjee et al. | 604/376 |
| 3,971,379 | 7/1976 | Chatterjee | 604/374 |
| 4,020,271 | 4/1977 | Chatterjee | 604/368 |
| 4,051,086 | 9/1977 | Reid | 604/376 |
| 4,136,697 | 1/1979 | Smith | 604/376 |
| 4,405,324 | 9/1983 | Cruz, Jr. | 604/376 |
| 4,481,076 | 11/1984 | Herrick | 162/9 |
| 4,481,077 | 11/1984 | Herrick | 162/9 |
| 4,543,410 | 9/1985 | Cruz, Jr. | 604/374 |

FOREIGN PATENT DOCUMENTS 810351 4/1969 Canada ..................... 604/374

*Primary Examiner*—C. Fred Rosenbaum
*Assistant Examiner*—Jerome R. Smith, Jr.

[57] ABSTRACT

Absorbent, retentive pulp is described which is capable of retaining good absorbency even after having been highly compressed. The pump is produced by subjecting a microfibrillated pulp slurry to pore generation by means of freezing and solvent exchange and to cross-linking with a cross-linking agent.

7 Claims, No Drawings

CROSS-LINKED PORE CONTAINING MICROFIBRILLATED CELLULOSE PREPARED BY FREEZING AND SOLVENT EXCHANGE

BACKGROUND OF THE INVENTION

This invention relates to absorbent, retentive cellulose pulp which is capable of retaining good absorbency even after having been highly compressed. This pulp is provided for use in absorbent products such as sanitary napkins, catamenial tampons, diapers, dressings or the like which are used for absorbing body fluids.

For many years, cellulose pulp has been utilized for absorbing body fluids. Wood pulp has been found most suitable for such products primarily because it is an inexpensive, readily available absorbent material. Such wood pulp is generally derived from soft wood trees such as southern pine and the like and is commercially treated in chemical pulping processes such as the kraft or sulfite processes during which the trunks and branches of trees are reduced to wood pulp fibers and non-fibrous substances such as gums, resins and lignin are chemically removed. The resulting wood pulp is sometimes bleached and then formed into board for subsequent disassocation into pulp fluff to be used in the aforementioned products.

Although pulp fluff derived from the conventional process steps has, in the past, been successfully employed in body fluid absorption products, the art has increasingly sought to improve the absorption capacity and fluid retention properties of wood pulp. Many suggestions have already been advanced, generally directed towards chemical modifications of the cellulose polymer of which the wood pulp fibers are composed. While these efforts have met with some success, the resulting products are substantially more expensive than native wood pulp and suffer from some peculiar drawbacks such as brittleness or slow wicking rates.

It has long been known that the absorbency of cellulosic fibers may be improved by wet cross-linking the fibers. Thus U.S. Pat. No. 3,241,553 discloses such cross-linking in order to provide absorbent fibrous products which have improved absorbency as well as the ability to retain greater amounts of absorbed fluids when subjected to pressures which tend to squeeze out the fluids absorbed. There is, however, no disclosure in said U.S. Pat. No. 3,241,553 concerning the cross-linking of microfibrillated fibers.

The need for a relatively inexpensive, simple process for treating native cellulose fibers to increase their absorption capacity and fluid retention properties has been met to a limited degree by the process disclosed by Chatterjee, et al. in U.S. Pat. No. 4,474,949. Chatterjee, et al. disclosed a process of mechanically beating a dispersion of cellulose fibers to a degree such that at least the outermost of the secondary walls of the cellulose fibers were essentially completely disintegrated to microfibrillar form followed by the freeze drying of the beaten dispersion. The resultant material possesses excellent absorption properties at low densities, but poor absorption properties at higher densities. In addition, the mechanical strength of this material is too low since it collapses in contact with water under a confining pressure. Furthermore, the sublimation step of freeze-drying requires a considerable amount of time. In fact, the lab production time of the process of U.S. Pat. No. 4,474,949 is approximately 90 hours.

Accordingly, there is a need for a much faster relatively inexpensive simple process for treating native cellulose fibers to increase their absorption capacity and fluid retention properties, not only at low densities but also at higher densities. The lab production time for such a process should not exceed about 8 to 10 hours.

SUMMARY OF THE INVENTION

In accordance with the objects and principles of the present invention a highly absorbent retentive cellulose fiber is provided, which fiber retains good absorbency and retention even after having been highly compressed. The process of the present invention can be carried out in the lab in about 8 hours.

The absorbent retentive pulp of the invention is produced by forming a dilute aqueous slurry of cellulose fibers and extensively beating the slurry to a degree such that at least the outermost of the secondary walls of the cellulose fibers are essentially completely disintegrated to microfibrillar form. The beaten dispersion is then frozen by the application of refrigeration means. Thereafter, the resultant frozen cake is subjected to solvent exchange with a non-aqueous solvent. A cross-linking agent is then added to the pulp. This is followed by evaporating the non-aqueous solvent and curing the pulp. Preferably, the pulp is then pressed in order to produce a densified thin sheet. The structure of the cellulose pulp derived from the teachings of this invention is similar to that disclosed in U.S. Pat. No. 4,474,949, which is incorporated herein by reference. If the pulp is examined under the microscope prior to compression, the fibrils released from the starting cellulose fibers by the beating step appear to be in the form of discrete platelets or sheets comprising said freed fibrils in compressed form. The sheets tend to appear as discontinuous walls surrounding and defining cellular voids. Although the microscopic structure of the product of the present invention is similar to that of the product of U.S. Pat. No. 4,474,949, nevertheless the cross-linking step of the present process provides a pulp which has a surprisingly increased absorption capacity and fluid retention even after having been highly compressed, the cross-linking having formed intermolecular cross-links between macromolecular chains. Said compressed product is also highly resilient (demonstrating a Z direction swelling) in the wet state. The express "Z direction" as used herein is intended to signify the direction of initial compression of the compressed product.

DETAILED DESCRIPTION OF THE INVENTION

In accordance with the invention an aqueous dispersion of fibrous cellulose is beaten to an extensive degree to free microfibrils from the fibrous structure.

While the preferred form of the starting cellulose fibers is chemical wood pulp derived from such pulping processes as kraft or sulfite pulping, it will be understood that almost any source of cellulose fibers is suitably employed. Accordingly, in addition to wood pulp, such diverse sources of cellulose fibers may include hemp, baggase, cotton and the like.

Irrespective of the plant source, cellulose fibers comprise cellulose chains, consisting of cellobiose units, laid down in a parallel arrangement with the long chained molecules strongly associated through secondary forces e.g. hydrogen bonds. This association of the cellulose chains results in a very uniform crystalline structure known as micelles or microcrystallites. The micelles are associated in the plant into long thread-like structures known as microfibrils. The association of the micelles into microfibrils is such that spaces or dislocations exist between micelles; such spaces, being of the order of about 15-20 angstrom units (A°), allowing liquid to migrate into the microfibril and accounting for at least part of the absorbency and retention properties of the cellulose fiber. High magnification photographs show that microfibrils of wood cellulose are filaments about 35 A° in breadth with a periodic variation in electron density along their lengths. Based on this observation, it has been proposed that the wood pulp microfibril is in the shape of a flat ribbon wound in the form of a tight helix.

The cellulose fiber itself is composed of layers of associated microfibrils. The outer layer is termed the primary wall and the inner layers are termed secondary walls which are further classified as $S_1$, $S_2$ layers, etc.

As described above, it is known, in the art of making paper, to beat or mechanically work a fiber slurry to free some microfibrils on the very outer layer of the cellulose fiber. The purpose of this beating treatment in the paper art is to enhance bonding. Great care, heretofore, has been taken to avoid damaging the inner layers.

In accordance with the teachings of U.S. Pat. No. 4,474,949, such a beating step is carried further to the point where at least the outermost of the secondary walls is essentially completely disintegrated to microfibrillar form. Preferably, the starting cellulose fibers are first dispersed in a dilute aqueous slurry. Such a slurry should have a solid content ranging from about 0.5 to about 10.0% and still more preferably, from about 1.5 to about 6.0%.

The slurry is next passed to a beating station where it is mechanically worked to free microfibrils to a suitable degree. The method and apparatus for beating the slurry are not critical provided that a sufficient degree of microfibrillation is accomplished. Accordingly, commercially available equipment such as the Hollander, Jordan, or disk refiner type of beaters may be employed. The Hollander beater is an apparatus wherein the slurry is introduced into a tub and forced to pass under the nip formed between a corregated roller and a plate. As the roller is turned, a shearing force is exerted on the fibers in the nip. The Jordan type of beater employs two nesting cones with an annular space in between. The inner cone reciprocates so that the slurry, introduced into the annular space, is sheared. In the disk refiner, two round plates are in a face to face relationship and at least one of the plates is provided with ribs and at least one of the plates rotates. The slurry is introduced between the faces of the plates and is sheared by the rotating action. There exists still other suggestions for producing microfibrillar pulp and these are equally useful in carrying out this invention. One such suggestion is found in U.S. Pat. No. 4,374,702 issued on Feb. 22, 1983 to Turbak, et al.

It has been found that sufficient beating has occurred when the resulting fibers have been reduced to a Canadian Standard Freeness value of less than 100 and preferably less than 50. The period of time during which a slurry of a particular dilution, with a particular type of fiber is beaten in a particular beating apparatus is easily correlated to the Canadian Standard Freeness value of the finished product by a series of simple experiments. It will be understood that because the parameters which effect beating time may vary greatly and still produce a beaten slurry usable in accordance with the teachings of this invention, no generalization can be made with respect to such beating time.

In said U.S. Pat. No. 4,474,949, when using a Valley Beater, Model No. 73-13-1-1/2 Niagra, obtained from the Voith Company of Appleten, Wis. and beating a slurry of loblolly pine bleached kraft pulp having a solid content of 2%, suitable beating times ranged from 120 to about 160 minutes.

The microfibrillated pulp, utilized in accordance with the present invention may also be prepared by soaking a southern pine bleached kraft pulp board with water and beating it on a Valley Beater at a consistency of 2%.

Thereafter, the beaten slurry is subjected to freezing by means of refrigeration, dry ice or liquid nitrogen. The frozen cake is then placed in a bath containing a non-aqueous solvent such as acetone, until the ice is melted. This solvent exchange may be conducted with a broad range of solvents. Among suitable solvents for this purpose are ethyl alcohol, butyl alcohol, pyridine, butyl acetate and benzene. Thereafter the thawed structure is washed a number of times with the solvent. A cross-linking agent is then added to the resultant solvent suspension and cross-linking is permitted to commence. Thereafter the non-aqueous solvent is evaporated followed by curing in an oven, whereby a highly absorbent, retentive cross-linked cellulose pulp results. In accordance with the cross-linking procedure, such as that taught by U.S. Pat. No. 3,241,553, cellulosic fibers are subjected to a chemical treatment whereby they are chemically modified to form bonds between the hydroxyl groups in the cellulose molecules. The reactive groups of the cross-linking agent which combines with the hydroxyl groups may exist prior to the reaction with cellulose, as in the case of glyoxal or they may be generated during the reaction of the cellulose, as in the case of the sodium thiosulfate derivative of divinylsulfone. In order to cross-link cellulose, the cross-linking agent must be at least difunctional with respect to cellulose, e.g., it must react with at least 2 hydroxyl groups. Formaldehyde, for example, is monofunctional with regard to many substances; it is, however, difunctional with respect to cellulose and is therefore a suitable cross-linking agent. Cellulose may be dry cross-linked or wet cross-linked. However, the procedure utilized in accordance with the present invention is wet cross-linking. A common technique known in the art is to apply the cross-linking agent and a catalyst to the cellulose in an aqueous bath, driving off the water in a drying step, and reacting the cross-linking agent with the cellulose in a subsequent curing step. However, in accordance with the present invention the cross-linking agent is added to the cellulose suspended in a non-aqueous solvent, which is then evaporated and the pulp is heat cured. The expression "heat curing" as used herein is intended to signify cross-linking by application of heat.

Wet cross-linked cellulose is obtained when the cross-linking agent is reacted with the cellulose while the cellulose fibers are not collapsed but are in a swollen state. Ordinarily the cellulose fibers are maintained in a swollen state by water which is present during the reaction. However, techniques have been developed whereby the cellulose fibers can be maintained in a swollen state in the absence of water by using in lieu thereof an inert, non-volatile substance. Cellulose fibers so treated have the properties of wet cross-linked cellulose even though the reaction takes place in the absence of significant amounts of water.

Suitable agents for the cross-linking of cellulose are formaldehyde, difunctional aldehydes such as glutaraldehyde; dichloro acetic acid, dichloro propanol-2, diepoxides, such as butadiene diepoxides and polyepoxides such as the compound marketed by Shell Chemical Company under the name Eponite 100, N-methylol acrylamide, and divinylsulfone. Most of the above materials require alkaline catalysts, such as sodium hydroxide, to produce wet cross-linked cellulose. However, for the purposes of the present invention, the preferred cross-linking agent is glutaraldehyde, the preferred catalyst utilized in conjunction therewith being zinc chloride. Glutaraldehyde is used in many medical devices (as for instance the device disclosed in U.S. Pat. No. 4,274,410). Zinc chloride was chosen because it not only permits the cross-linking or/polymerization to occur, but it also causes swelling of cellulose which imparts higher resilient characteristics to the final product.

Additional wet cross-linking agents include: condensation products of formaldehyde with organic compounds, such as urea or other chemical compounds which contain at least two active hydrogen groups, particularly dimethylolurea, dimethylol ethyleneurea and imidazolidine derivatives; dicarboxylic acids; dialdehydes such as glyoxal; diisocyanates; divinyl compounds; dihalogen-containing compounds such as dichloracetone and 1,3-dichloropropanol-2; and halohydrins such as epichlorohydrin etc.

The fibers are in a swollen state at the time of cross-linking in order to obtain wet cross-linked cellulose. Although the swelling is generally achieved in accordance with the prior art by cross-linking in the presence of water, other swelling agents may be used, such as the preferred zinc chloride referred to above.

Cellulose molecules consist of a large number of glucose units linked to each other through glucoside linkages (oxygen bridges). The preferred catalyst, zinc chloride, reacts with glucoside linkages to form an oxonium salt. This reactive product is more polar and enables the non-reactive cellulose to swell to a greater degree.

One of the preferred cross-linking agents of the present invention, namely glutaraldehyde, undergoes a condensation reaction with cellulose with the loss of water to form an intermolecular cross-link between macromolecular chains. The reaction of cellulose with glutaraldehyde takes place through the formation of hemiacetal and acetal linkages. The addition of glutaraldehyde in the presence of zinc chloride, to the beaten pulp slurry causes the formation of polyglutaraldehyde and the commencement of the cross-linking of cellulosic fibers. Good results have also been obtained, in accordance with the present invention when 37% W/V of formalin was used in place of glutaraldehyde as the cross-linking agent.

The initial freezing of the slurry, prior to the solvent exchange, may be effected by passing the slurry into an externally refrigerated compartment and retaining the slurry therein until frozen. Alternatively the slurry may be circulated around the source of refrigeration such as cooling tubes or a bath containing coolant, e.g., liquid nitrogen, dry ice, alcohol solution or the like and the frozen slurry collected.

After the solvent exchange and cross-linking steps, the resultant product is a sponge-like dried pulp which, either in the sponge-like state or when ground into pulp fluff, exhibits a substantial increase in liquid absorption and retention properties as contrasted with pulp provided by conventional means. In addition, after the final dried product is pressed under high pressure in order to form a thin flat sheet, the resultant pressed product is capable of retaining good absorbency and retention and thus differs substantially from the product of U.S. Pat. No. 4,474,949 which does not include the solvent exchange step or the cross-linking step.

If an electromicrograph of the cross-linked, pore containing microfibrillated cellulose, prepared in accordance with the present invention is examined, it could be seen that the pulp comprises sheets or platelets of microfibrils. These sheets are of a random shape and appear to form somewhat discontinuous walls surrounding relatively large voids. The platelets are almost leaf-like in structure and are similar to those as illustrated in U.S. Pat. No. 4,474,949.

The platelets vary in their largest dimension from about 2 microns to about 130 microns with 70 microns being typical. The platelets are no more than about 5 microns thick and typically about 2 microns thick. The platelets surround void areas having a largest dimension value of less than about 500 microns.

It is believed that the morphology of the pulp of this invention results from the fact that when the fibrillated invention results from the fact that the fibrillated pulp is subjected to freezing the ice crystals compress the fibrils between crystal facets into flat sheets. The solvent exchange step does not disturb this configuration.

The invention will be further described by reference to the following example wherein there is disclosed a preferred embodiment of the present invention. However, it is to be appreciated that such example is illustrative but not limitative of the broader aspects of the inventive concept.

The percentages of ingredients in the slurry are given herein as weight of the ingredient in grams for each 100 ml of slurry.

EXAMPLE 1

The raw material was prepared by soaking a southern pine bleached kraft pulp board with water and beating it on a Valley Beater at a consistency of 2%. The Valley Beater, Model No. 73-13-1-1/2 Niagra, obtained from the Voith Company of Appleton, Wis., consists of an oval, open cast-iron tub, beater bars and bed plate. The stock is moved counterclockwise by rotation of the beater bars (500 ±10 rpm). The beating action takes place between bars and the bed plate. In order to prepare the raw material, initially, about 430 grams of air-dried pulp board (6.5% moisture) were soaked in 10 liters of water for a minimum of 4 hours. The pulp boards were than cut into small pieces and processed in the Valley Beater with an additional 10 liters of water for 10 minutes (no beating) to prepare a slurry of 2% consistency. The beating process, started by applying a load to the beater bars, was continued for a period of 4 hours. The beaten slurry was then placed in a reaction vessel and heated to 80° C. The reaction vessel is a unit manufactured by Dover Corporation. The unit (Model No. TA-40-SP-1972) is constructed of stainless steel and it is steamed jacketed for heating at maximum water pressure of 25 psi at 300° F. The maximum capacity of this unit is 100 liters. Mixing was carried out by a wall scraper. The beaten slurry was then poured into a container and frozen to −25° C. for 24 to 72 hours as required. The freezing time was dependent on sample thickness. The freezer used was an upright frost-free freezer (model number 16-OF16K) manufactured by Amana. The maximum low temperature capability of the unit is −25° C. The frozen cake was then placed in an acetone bath until the ice was melted. Then the thawed structure was washed three more times with acetone. Based on each gram of the oven-dried weight of fiber, 0.4 g of zinc chloride and 0.25 mils of glutaraldehyde (50% in water) were mixed in enough acetone to cover the structure. After evaporation of acetone, the structure was cured in a 100° C. oven for 1 hr. The low density cross-linked structure was washed in tap water for 15 minutes, excess water removed and dried in a 105° C. oven for 30 minutes. The final dried material was pressed to 5,000 psi. The press which was utilized is manufactured by Wabash Metal Products Company. It has a controlled heating system and possesses a 6-inch compression stroke and maximum compression force of 30 tons. The upper and lower plenums have the capability of heating to 300° C.

For the purposes of the following discussion, the product of Example 1 is designated at MFCS-III meaning microfibrillated cellulose sheet-III. The product of U.S. Pat. No. 4,474,949 prepared by microfibrillation and freeze drying, but without cross-linking, is designated as MFCS-I.

The product of Example 1 was then tested for absorption properties at different densities by the porous plate method. (Table 1).

The Porous Plate Testing apparatus, is described in detail in Textile Res. J. 37 pp. 356–366, 1967, and a modified testing procedure has been further described as "Gravimetric Absorbency Testing System" in a monograph on "Absorbency" in Textile Science and Technology, volume 7, page 67, edited by Pronoy K. Chatterjee, published in 1985 by Elsevier Science Publishers BV, P.O. Box 211, 1000 AE Amsterdam, The Netherlands. Briefly, this test involves placing the sample in what is essentially a Buchner Funnel having a porous bottom plate and holding the sample in place by applying thereon a standard weight to maintain a standardized confining pressure. The porous plate is placed in contact with a reservoir of fluid and the sample is allowed to absorb the fluid through the porous plate until saturated. By maintaining the samples at essentially the level of the reservoir, the fluid absorbed is subjected to essentially zero hydraulic head with respect to the reservoir. The weight of fluid absorbed, divided by the weight of the sample, is termed the Maximum Capacity. As the sample absorbs fluid, a measurement of weight absorbed as a function of time is made. The slope of this curve at the time absorption begins is termed the Initial Rate of Absorption. To determine fluid retention, the saturated sample is elevated with respect to the reservoir, thereby imposing a hydraulic head upon the fluid absorbed, the head being arbitrarily chosen as 35.5 cm. of fluid. The apparatus is provided with means for measuring the weight of fluid retained under the hydraulic head. Retention values are reported as the weight retained per unit weight of sample. The results of testing the samples are recorded below in Table 1. The testing fluid in each case is a 1% NaCl aqueous solution, and the confining pressure is 4.8 grams/cm$^2$.

TABLE 1

EVALUATION OF MICROFIBRILLAR CELLULOSE
Method: Porous Plate Test With
1% Aqueous NaCl
Sample Density: 0.4 g/cm$^3$

| Sample | Process | Absorbency Max Cap. (g/g) | Ret'n (g/g) | Z Direction Expansion % |
|---|---|---|---|---|
| Filter Paper | Control No freeze drying No X-link, No beating | 3 | 2 | 0 |
| Fluff Pulp | Control No freeze drying No X-link No beating | 5 | 3 | 0 |
| MFCS-I | Freeze-dried (Control, no X-link) | 6 | 5 | 0 |
| Fluff Pulp | Freeze-dried (X-link) No beating | 10 | 3 | 200 |
| MFCS-III | Solvent Exch. (X-link) | 16 | 8 | 400 |

As can be seen from Table 1, the product of the present invention as set forth in Example 1 (designated MFCS-III) is compared with filter paper and fluff pulp controls which have neither been freeze dried nor cross-linked; freeze dried non-beaten fluff pulp as well as the product of U.S. Pat. No. 4,474,949 (designated MFCS-I) which consists of non cross-linked freeze-dried microfibrillated wood pulp cellulose.

The conditions under which the pulp control were produced, were similar to the corresponding conditions for preparing the product of Example 1, except as noted in Table 1.

The results in Table 1 indicate that after the materials were densified by pressing to 0.4 g/cc, MFCS-III (product of present Example 1) achieved high absorbency (16 g/g). It is evident from the data in Table 1 that the densified cross-linked microfibrillated cellulose pulp of the present invention is significantly superior in absorption and retention than its non cross-linked counterpart MFCS-I disclosed in U.S. Pat. No. 4,474,949. Cross-linking a non-fibrillated fluff pulp also improves the absorption capacity, but not to the extent that could be achieved by the microfibrillated batch. In this connection it will be noted that the maximum capacity of MFCS-III at 0.40 g/cm$^3$ density is 16 g/g while the maximum capacity at 0.4 g/cm$^3$ density of MFCS-I is only 6 g/g, i.e., almost three times as great. It is thus very surprising that the process of the present invention provides such an extraordinary improvement over the process of U.S. Pat. No. 4,494,949.

While Table 1 indicates that a significant improvement was obtained with a density level of 0.4 g/cm$^3$. improvements have also been found to be quite evident at a density level of 0.1 g/cm$^3$ or higher. Normally a 0.5M solution of cupriethylenediamine is a good solvent for cellulose, but if cross-linking is present, the latter solvent will not dissolve the cross-linked product. Following the Tappi method T-230 for viscosity measurements, it was observed that the MFCS-I and virgin wood pulp easily dissolved in cupriethylenediamine but the product of the present Example 1 namely MFCS-III does not dissolve therein. This phenonmenon indicates the occurrence of cross-linking in the latter case.

The product of present Example 1 (namely MFCS-III) may be utilized to increase the total absorption capacity of napkins and also to increase the wicking properties of napkins and tampons. MFCS-III also demonstrates a uniaxial Z direction swelling in the wet state of 400% as can be seen from Table 1.

The fast wicking rate of the product of present Example 1 allows the fluid to be transported to all regions of napkins. The fast wicking is mainly due to densification of the MFCS-III. The densification reduces both the void volume and pore size. However, as soon as the fluid hits a certain spot the capillary size at that spot will increase. Hence the fluid front is moved rapidly through the large capillaries to the adjacent smaller capillaries.

The compressability of the MFCS-III in the dry state and its Z direction swelling in the wet state causes this material to be especially suitable for tampon applications.

From the above Table 1 it will be noted that densified microfibrillated cross-linked cellulose (MFCS-III) showed significantly higher fluid absorption and retention capacities than unbeaten or fibrillated non-cross-linked freeze-dried wood pulp. The increase in surface area of the fibers obtained by beating coupled with freezing and solvent exchange increased the retention capacity. The fast wicking rate with Z direction swelling is attributed to chemical cross-linking of these fibers at low densities followed by their densification in the final dry state. Densification of the MFCS-III produces a flat, flexible board. Upon wetting, this board expands to a foam-like structure which has an enormous void volume available for liquid absorption.

While the invention has been described in terms of producing a highly absorbent cellulose pulp, nothing herein should be construed to suggest that the cellulose fibers cannot be otherwise additionally treated by other means to further enhance absorbency combined with other components to produce a composite material for absorbent purposes. Such modification, as well as others which will occur to one skilled in the art, are all within the scope of teachings of this invention.

We claim:

1. A process for preparing a highly absorbent retentive cellulose pulp, said absorbent element being capable of retaining good absorbency even after having been highly compressed, said process comprising:
   (a) forming an aqueous slurry of cellulose fibers;
   (b) extensively beating said slurry to a degree such that at least the outermost of the secondary walls of said cellulose fibers are essentially completely disintegrated into microfibrillar form;
   (c) freezing said slurry;
   (d) submitting the resultant frozen cake to solvent exchange with a non-aqueous solvent;
   (e) adding a cross-linking agent to the pulp;
   (f) evaporating said non-aqueous solvent and heat curing said pulp, whereby said highly absorbent, retentive pulp results.

2. The process of claim 1, which comprises additionally compressing said absorbent element to produce a densified thin sheet having a sample density of at least about 0.1 g/cm$^3$.

3. The process of claim 2, said absorbent element having been densified under pressure to a sample density of at least about 0.4 g/cm$^3$.

4. The process of claim 1, in which said cross-linking agent is selected from the group consisting of glutaraldehyde, formalin and a polyamine/amide epichlorohydrin adduct.

5. The process of claim 1, in which said cross-linking agent is glutaraldehyde, catalyzed by zinc chloride.

6. The process of claim 1, in which said non-aqueous solvent is selected from the group consisting of acetone, ethyl alcohol, butyl alcohol, butyl acetate, pyridine and benzene.

7. The process of claim 6, in which said non-aqueous solvent is acetone.

* * * * *